(12) United States Patent
Devitt et al.

(10) Patent No.: US 6,874,932 B2
(45) Date of Patent: Apr. 5, 2005

(54) METHODS FOR DETERMINING THE DEPTH OF DEFECTS

(75) Inventors: John William Devitt, Maineville, OH (US); Anthony S. Bauco, Horseheads, NY (US); Craig Alan Cantello, Schenectady, NY (US); Kevin G. Harding, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/609,812

(22) Filed: Jun. 30, 2003

(65) Prior Publication Data

US 2004/0262521 A1 Dec. 30, 2004

(51) Int. Cl.[7] .............................................. G01N 25/72
(52) U.S. Cl. ........................ 374/5; 374/121; 250/341.6
(58) Field of Search ............................ 374/4, 5, 7, 45, 374/57, 120, 121; 250/341.1, 341.6, 342

(56) References Cited

U.S. PATENT DOCUMENTS

| | | | |
|---|---|---|---|
| 4,266,185 A | | 5/1981 | Charlesworth et al. |
| 4,345,457 A | | 8/1982 | Kuroki et al. |
| 4,557,607 A | | 12/1985 | Busse |
| RE32,166 E | | 6/1986 | Berge |
| 4,647,220 A | | 3/1987 | Adams et al. |
| 4,760,304 A | | 7/1988 | Oliver |
| 4,826,326 A | | 5/1989 | Reynolds et al. |
| 4,983,836 A | * | 1/1991 | Matoba et al. .................. 374/5 |
| 5,111,048 A | | 5/1992 | Devitt et al. |
| 5,302,830 A | * | 4/1994 | Shivanandan ................ 250/342 |
| 5,748,003 A | | 5/1998 | Zoughi et al. |
| 5,810,477 A | * | 9/1998 | Abraham et al. ............... 374/4 |
| 6,236,049 B1 | * | 5/2001 | Thomas et al. .......... 250/341.6 |
| 6,437,334 B1 | * | 8/2002 | Thomas et al. .......... 250/341.6 |
| 2002/0018510 A1 | * | 2/2002 | Murphy et al. ................ 374/57 |
| 2004/0114662 A1 | * | 6/2004 | Messler ....................... 374/130 |

OTHER PUBLICATIONS

"Infrared Detection of Fatigue Cracks and Other Near–Surface Defects," by Kubiac, *Applied Optics*, vol. 7, No. 9, Sep. 1968.

"Coating Tolerant Thermography for the Detection of Cracks in Structures," by Lesniak, et al., *NDT Solution*, Sep. 1997.

"Detection of Open Cracks by a Photothermal Camera," by Legrandjacques, et al., *Review of Progress in Quantitative Nondestructive Evaluation*, vol. 17, 1998.

"Flying Laser Spot Thermal Wave IR Imaging of Horizontal and Vertical Cracks," by Wang, et al., *Review of Progress in Quantitative Nondestructive Evaluation*, vol. 9, 1990.

"Thermal Wave Imaging of Closed Cracks in Opaque Solids," by Grice, et al., *J. Appl. Phys.*, 54 (11), Nov. 1983.

* cited by examiner

*Primary Examiner*—G. Bradley Bennett
(74) *Attorney, Agent, or Firm*—Fletcher Yoder

(57) ABSTRACT

A method facilitates inspection of a component surface. The method comprises positioning a surface of the component to be inspected in an optical path of at least one infrared radiation detector, heating the component surface using electromagnetic radiation to cause an increase in radiance from a defect present at the component surface, and detecting temperature variations within the component surface using the at least one infrared radiation detector, such that the surface irradiance is measured at predetermined locations across the component surface. The method further comprises detecting cracks in the component by analyzing radiation transient response data received by the infrared radiation detector, and correlating the temperature variations to the radiation transient response data to determine a depth of the detected cracks.

20 Claims, 3 Drawing Sheets

METHODS FOR DETERMINING THE DEPTH OF DEFECTS

BACKGROUND OF THE INVENTION

This application relates generally to the detection of fatigue cracks in materials and, more particularly, to methods for detecting fatigue cracks in gas turbine components.

Vibratory, mechanical, and thermal stresses induced to an aircraft may cause fatigue cracks to develop in a variety of components. More specifically, low cycle fatigue (LCF) cracks may develop in any component that is subjected to cyclic stresses. Over time, continued operation with fatigue cracks may lead to component failures as the cracks propagate through the component. Detecting the cracks early in their growth may facilitate reducing component failures.

At least some known nondestructive evaluation (NDE) methods for inspecting components for fatigue cracks or other defects which could cause a failure of the engine or airframe, include for example, surface wave ultrasonic testing, eddy current testing, and fluorescent penetrant inspection (FPI). Generally, none of the known NDE methods are considered to be singularly capable of detecting LCF cracks with sufficient reliability, ease of application, and with reduced environmental, health, and safety (EHS) concerns. More specifically, unique geometries of some components may restrict the evaluation techniques that can be utilized, and at least some known methods are susceptible to errors and false indications from contaminants on the surface of the component being inspected, or contaminants within the cracks or defects. Additionally, at least some known NDE methods may inaccurately indicate a defect from surface roughness and other surface anomalies which do not result in component failure. In particular, craze cracking of coatings may cause multiple false indications using at least some known NDE methods.

To facilitate accurate more reliable results, without increasing EHS concerns, at least some components are inspected using infrared methods of NDE. Infrared NDE methods operate on the premise that all matter continuously absorbs and emits electromagnetic radiation. The continual motion of the charged particles within a material results in the emission of electromagnetic radiation. More specifically, the motion of the charged particles will increase with an increase in temperature and cause a corresponding increase in the continuous emission of radiation from the material. Cracks and defects typically absorb more radiation than other areas of the component, and as a result, the cracks also have a higher emissivity and radiance relative to the relatively flat and smoother surface areas surrounding the defect. However, such NDE techniques may not be able to distinguish between defects which could result in a failure and other minor surface anomalies which are not of great concern.

BRIEF SUMMARY OF THE INVENTION

In one aspect a method for detecting a crack extending into a component surface is provided. The method comprises positioning a surface of the component to be inspected in an optical path of at least one infrared radiation detector, heating the component surface using electromagnetic radiation to cause an increase in radiance from a defect present at the component surface, and detecting temperature variations within the component surface using the at least one infrared radiation detector, such that the surface irradiance is measured at predetermined locations across the component surface. The method further comprises detecting cracks in the component by analyzing radiation transient response data received by the infrared radiation detector, and correlating the temperature variations to the radiation transient response data to determine a depth of the detected cracks.

In another aspect a method for determining a depth of a crack in a component is provided. The method comprises positioning a surface of the component to be inspected in an optical path of at least one infrared radiation detector, such that the optical path is substantially normal to a plane parallel to the component surface, heating the component surface using electromagnetic radiation to cause an increase in radiance from a defect present in the component surface, such that the heat is applied to the component substantially normal to the component surface, and detecting temperature variations within the component surface using the at least one infrared radiation detector, such that the surface irradiance is measured at predetermined locations across the component surface. The method further comprises detecting cracks in the component by analyzing radiation transient response data received by the infrared radiation detector, and correlating the temperature variations to the radiation transient response data to determine a depth of the detected cracks.

DETAILED DESCRIPTION OF THE INVENTION

Figure 1:
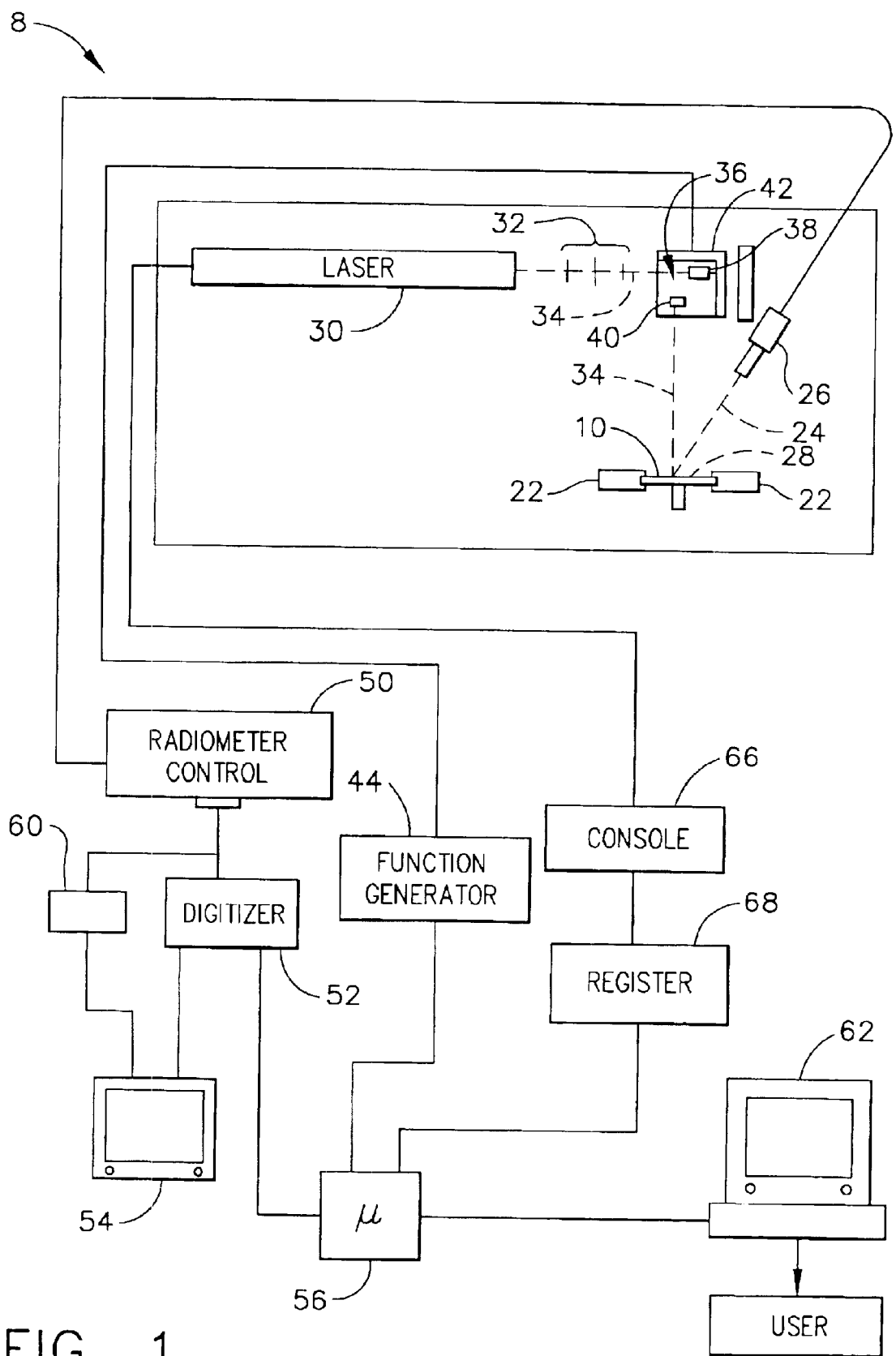
FIG. 1 is a schematic illustration of an exemplary nondestructive evaluation inspection system.
Figure 2:
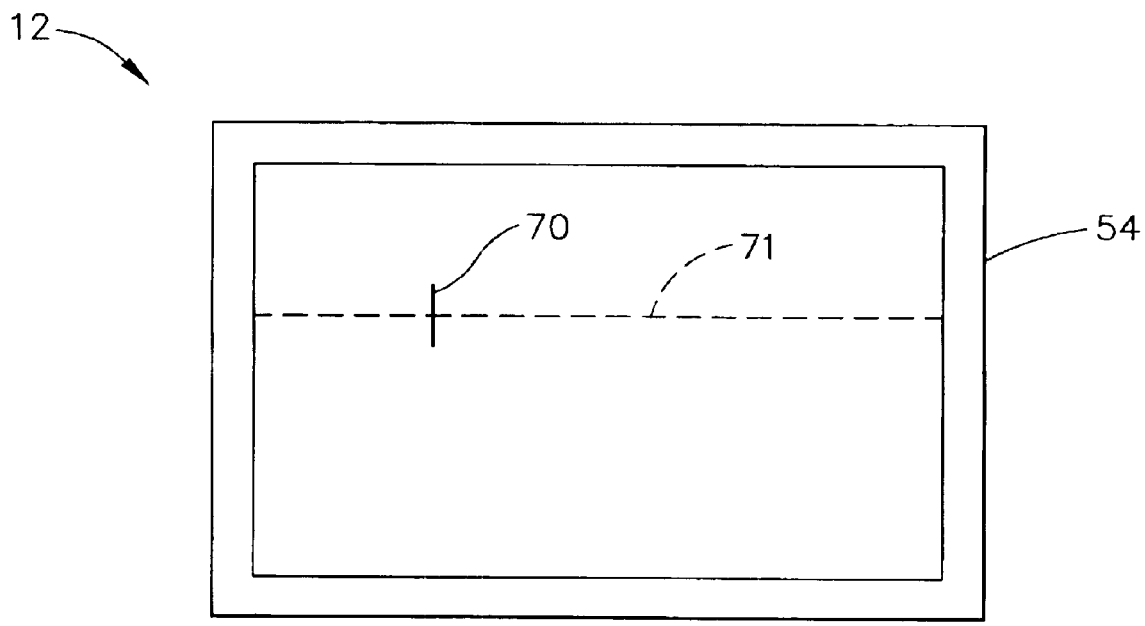
FIG. 2 is an exemplary illustration of an infrared video image of a portion of a component selected for inspection using the inspection system shown in FIG. 1.
Figure 3:
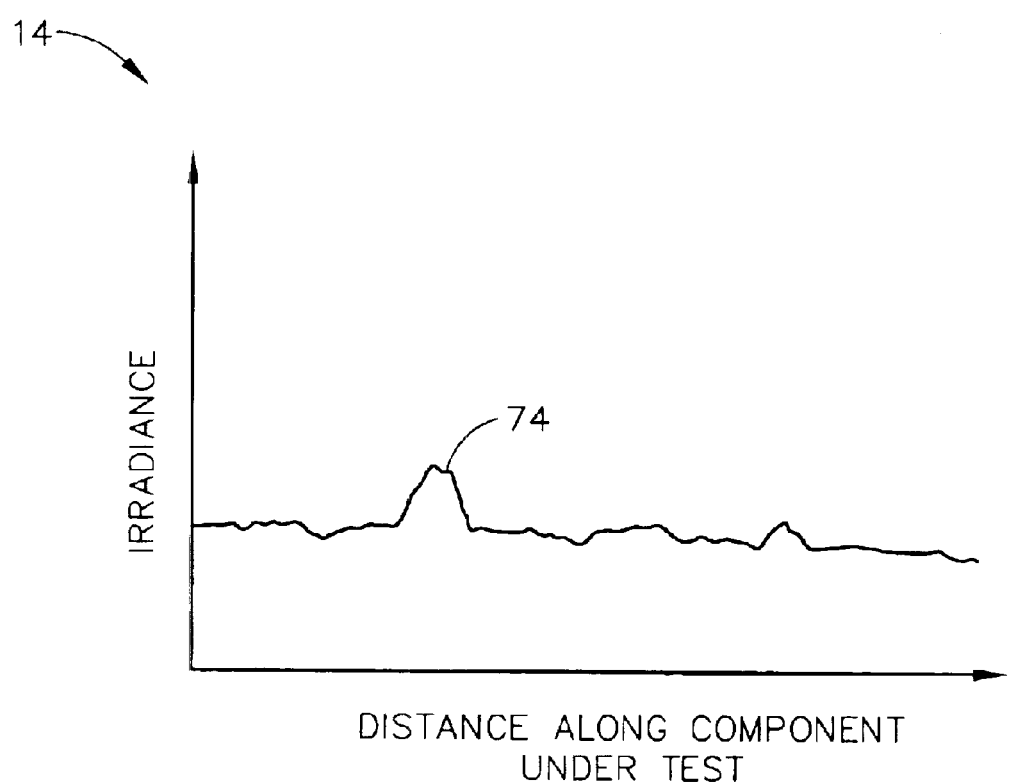
FIG. 3 is an exemplary illustration of a graph of radiance emitted from the component portion displayed in the infrared video image shown in FIG. 2, and at a predetermined uniform temperature.
Figure 4:
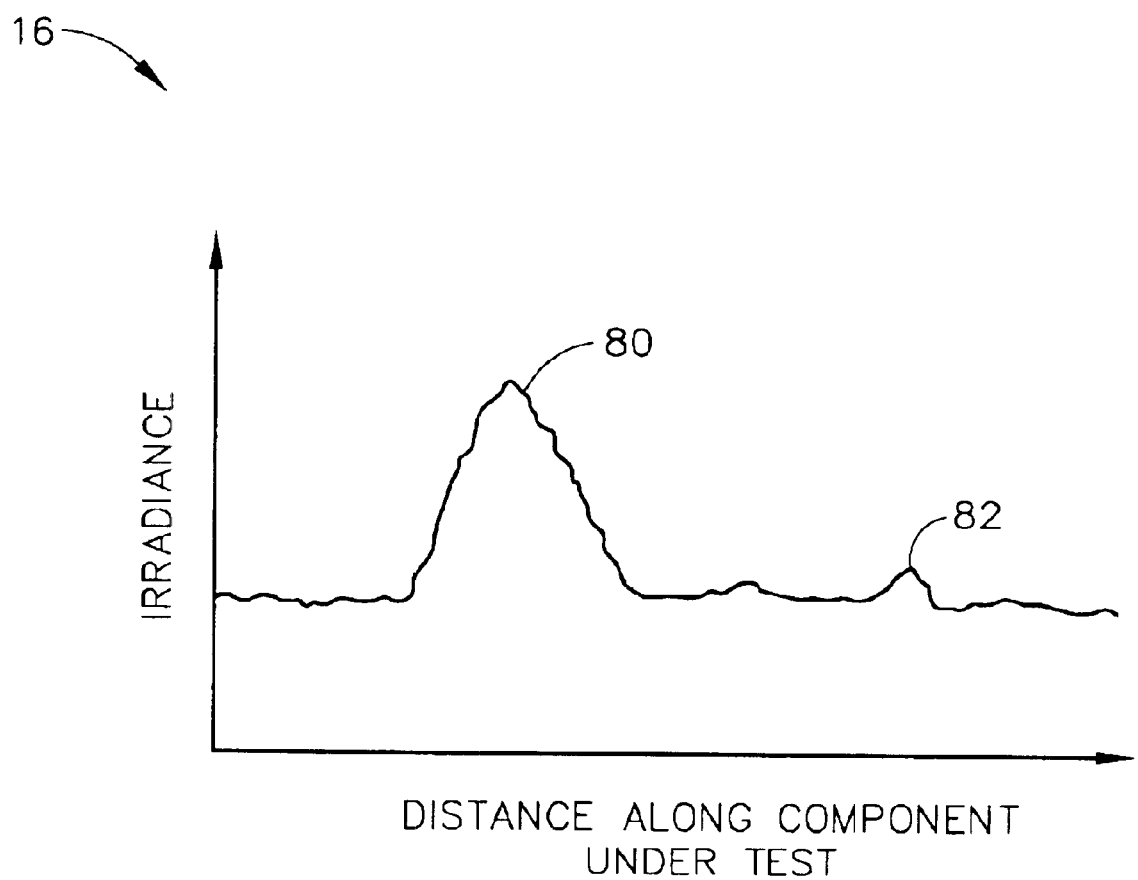
FIG. 4 is an exemplary illustration of a graph of the radiance emitted from the component portion displayed in the infrared video image shown in FIG. 2 and during scanning.

FIG. 1 is a schematic illustration of an exemplary nondestructive evaluation test system 8 that may be used to detect cracks or defects, and an associated depth of such cracks or defects, in a component 10. FIG. 2 is an exemplary illustration of an infrared video image 12 of a portion of component 10 being inspected. FIG. 3 is an exemplary illustration of a graph 14 of radiance emitted from the portion of component 10 displayed in infrared video image 12 shown in and at a predetermined uniform temperature. FIG. 4 is an exemplary illustration of a graph 16 of the radiance emitted from the portion of component 10 displayed in infrared video image 12 and during scanning, as described in more detail below. In the exemplary embodiment, component 10 is an aircraft component, such as, but not limited to a gas turbine engine component. Component 10 is secured for inspection within a fixture 22 such that component 10 is positioned within an optical path 24, or within the field of view of, at least one detector 26. In the exemplary embodiment, only one detector 26 is illustrated, but it should be noted that a plurality of infrared detectors 26 may be utilized. For example, detector 26 may be, but is not limited to being either an infrared radiometer and/or an infrared camera. In one embodiment, detector 26 is an infrared imaging radiometer commercially available from FLIR Systems, Inc., Billerica, Mass. More specifically, to facilitate defect detection, component 10 is positioned within fixture 22 such that optical path 24 is substantially normal to a plane parallel to a surface 28 of component 10 being inspected.

A laser 30 and focusing optics 32 provide a coherent scanning laser beam 34, which is used to heat selective portions of component surface 28 during inspection of component 10. More specifically, focusing optics 32 enable independent sizing and focusing of beam 34 while maintaining a high output. Focusing optics 32 work in conjunction with a mask in a Fourier plane to create a desired shape output for laser beam 34. In one embodiment, focusing optics 32 cause laser beam 34 to be focused in an S-shape while beam 34 is scanned across component surface 28. In another embodiment, focusing optics 32 cause laser beam 34 to be focused in a circular shape wherein a radius of the circle is expanded while laser beam 34 is scanned across component surface 28. In a further embodiment, focusing optics 32 cause laser beam 34 to be focused in a series of concentric circles while laser beam 34 is scanned across component surface 28. In an alternative embodiment, focusing optics 32 use a holographic element to cause laser beam 34 to be focused in a grid of circles. In yet a further embodiment, focusing optics 32 cause laser beam 34 to be spread at least partially across component surface 28 in a line.

Scanning laser beam 34 is focused onto component surface 28 using a known two-dimensional (2-D) scan mirror arrangement 36. In the exemplary embodiment, scan mirror arrangement 36 includes a first mirror 38, a second mirror 40, and at least one scanning device 42 which includes a plurality of known motion control devices (not shown) for controlling relative movement of each mirror 38 and 40, and of scanning laser beam 34 with respect to component 10 and fixture 22. In one embodiment, each scanning device 42 includes, but is not limited to including, motion control devices such as piezoelectric devices, and/or galvanometers. In the exemplary embodiment, fixture 22, detector 26, laser 30, and scan mirror arrangement 36 are each mounted on an optical table within a safety enclosure (illustrated schematically).

To facilitate optimizing detection of defects within components 10, and to facilitate distinction between defects and surrounding material within component 10, laser 30 and detector 26 are operated in different spectral bands. More specifically, in the exemplary embodiment, laser 30 is a YAG laser that is operated at a wavelength of approximately 1.06 microns, and detector 26 is operated at a selected wavelength band between approximately three microns and approximately twelve microns to facilitate minimizing false indications of defects caused by detector 26 sensing light reflected from component surface 28. Alternatively, if a broader band heating source is used that interferes with the detector 26, it may be necessary to detect radiation emitted from surface 28 after the heating source has been removed.

Laser 30 and scan mirror arrangement 38 are coupled to a known function generator 44 that generates signals for controlling scanning device 42. In the exemplary embodiment, function generator 44 generates analog signals for controlling each scanning device 42. More specifically, in response to signals transmitted from function generator 44, each scanning device 42 controls movement of mirrors 38 and 40 in an X-Y coordinate system, such that the substantially all of the selected portion of component surface 28 is scanned by laser beam 34 during inspection of component 10.

A radiometer control 50 is coupled to detector 26 for adjusting the focus and contrast of detector 26. Radiometer control 50 is coupled to an image digitizer 52 which is coupled to a video display 54. A processor 56 controls execution of system 8 and is coupled to radiometer control so, image digitizer 52, and video display 54. As used herein, the term "processor" refers to microprocessors, central processing units (CPU), application specific integrated circuits (ASIC), logic circuits, and any other circuit or processor capable of executing inspection system 8, as described herein. Processor 56 is also coupled to function generator function generator 44, laser 30, and focusing optics 32.

Image digitizer 52 is known and facilitates storage by processor 56 of a series of images 12 of radiance received from surface 28 for analysis of the transient response of the radiance, as described in more below. More specifically, image digitizer 52 includes software that facilitates enhancing the digitized signal created from the video image 12 provided by detector 26 to improve the detection ability of even the most minuscule of defects in component surface 28 as laser beam 34 is scanned across the surface. For example, in one embodiment, image digitizer 52 includes a data compression algorithm that in conjunction with specific detector level settings, i.e., camera black level settings, facilitates distinguishing deep cracks detected within component surface 28 from non-perpendicular cracks, as described in more detail below. In one embodiment, image digitizer 52 is a "DIGIMAX" image digitizer commercially available from Datacube, Inc., Massachusetts.

In the exemplary embodiment, an image recorder 60 is coupled between radiometer control 50 and video display 54 for recording the actual analog video images 12 received by detector 26 as laser beam 34 scans across component surface 28. For example, in one embodiment, image recorder 60 is a videocassette recorder. In another embodiment, images are stored on a digital data storage device, such as a computer hard drive, after the video signal has been digitized by image digitizer 52. More specifically, image recorder 60 facilitates enhanced analysis of video images 12 such that minor surface anomalies (indicated as 82) may be distinguished from defects which could result in failure of component 10.

Processor 56 is also coupled to function generator 44, laser 30, and focusing optics 32, such that inspection of component 10 may be preprogrammed and/or controlled by an operator through an input/output (I/O) driver register 68 coupled to processor 56. More specifically, laser 30 is coupled to processor 56 through a laser console 66 and an input/output (I/O) driver register 68. The combination of console 66 and register 68 enable the gating and power level of laser 30 to be preprogrammed by an operator via terminal 62. Adjusting the laser power density facilitates providing a distinguishing contrast between any defects and the material surrounding the defects, without damaging component 10 when surface area 28 is selectively heated by laser beam 34.

During an inspection of component 10, initially, component 10 is cleaned to facilitate reducing the emissivity of the portion of component surface 28 being inspected. Moreover, cleaning surface 28 facilitates removing coatings of any type, such as paints, and/or thermal barrier coatings that may occlude a defect, such that the detection ability of inspection system 8 is facilitated to be enhanced. After cleaning, component 10 is then mounted in fixture 22 in alignment with 2-D scan mirror arrangement 36 and detector 26, as described above.

Laser 30 is then positioned such that laser beam 34 is substantially incident upon component surface 28 as close to normal to surface 28 as possible for optimum defect detection. Surface 28 is then preheated by scanning with laser beam 34 to elevate an operating temperature of surface 28 substantially uniformly across the portion of surface 28 being inspected. Radioactive or electromagnetic, heating is employed rather than conductive or convective heating, to utilize the higher absorption, which is indicative of an amount of emissivity of a defect 70 relative to the surface area surrounding the defect during heating. A temperature difference created by the increased amount of energy absorption in the crack 70 produces an enhanced signal-to-noise ratio (SNR) or contrast between the defect 70 and surrounding surface area because the background dissipates most of the heat. More specifically, in non-cracked areas of surface 28, or those areas of surface 28 that do not include defects, the heat is dissipated outwardly across surface 28. A defect 70 will appear in video image 12 captured by detector 26.

Detector 26 and radiometer controls 50 can also be variably selected to generate graph 16 to illustrate the irradiance scanned along a variably selected line 71 extending at least partially across surface 28. Thus the radiance received by detector 26 while scanning across surface 28 can be measured at different locations across surface 28. Any defects 70 along surface 28 will appear as a peak 74 as shown in graph 14.

As laser beam 34 is scanned across preheated surface 28, selective, localized heating will occur as beam 34 passes. More specifically, laser beam 34 is scanned initially in a first direction across surface 28, and then rescanned in a second direction that is not the same as the first direction. The bi-directional scan facilitates distinguishing cracks 70 having a greater depth from non-perpendicular defects 70. Radiance emitted from surface 28 is detected by detector 26 and is graphically displayed on video display 54. More specifically, as laser beam 34 passes over defect 70, the radiance peaks (illustrated as 80 in FIG. 4) relative to graph 16 because of the higher absorption and emittance of defect 70 relative to the surrounding material. Thus, the detection ability of a defect 70 is enhanced by scanning with laser beam 34. More specifically, the series of infrared images 12 recorded and/or stored at each scan location facilitate analysis and observation of the transient response as the radiance received from defect 70 decays from peak 80, at the moment laser beam 34 is actually radiating defect 70, back to its original intensity level after scanning.

The series of images 12 are converted to a graphical form, similar to graphs 14 and/or 16 which collectively represent the transition or transient response of the radiance from defect 70 after laser scanning. Additionally, a computer-fitted calibration curve is generated based on images 12. A defect depth map is then generated based on the calibration curve. More specifically, the depth determination curve is generated after measuring the transient heat of cracks of varying depths cut into a sample piece of material fabricated with substantially uniform properties. The measured values are then compared to the actual values of the depth of the cracks, and the calibration curve is created using a "best-fit" exponential curve-fitting algorithm.

The amount or degree of decay between the peaks of successive images 12 over a selected time period is analyzed to distinguish between a defect 70, which could result in a failure of the component, and other minor imperfections 82 within the selected surface 28 of the component 10. The decay time for the transient response of a defect 70 which could cause a failure of component 10 is typically about two to four times as long as a minor surface anomaly 82, depending upon the size of defect or crack 70. The transient response of the radiance from surface 28 is analyzed to facilitate distinguishing between a minor surface anomaly 82 and defects 70 which could cause a failure of component 10.

One reason for the enhanced contrast between the defect or crack 70 and areas of component 10 surrounding defects 70 is due to the higher signal-to-noise ratio while defects 70 are under laser irradiation. The SNR value remains high immediately after scanning by laser beam 34, but decays back to the pre-laser scanning value at a given rate corresponding to the rate of decay of the intensity level of the radiance from the defect 70. Thus, the SNR value may also be used as a qualitative aid in distinguishing defects 70 from background artifacts within the component surface 28. In another embodiment, if the crack or defect is subsurface and proximate to surface 28, a stress is induced to component 10 to facilitate detecting such defects at the component surface.

Generally, the basis of the inspection system is that a defect or crack 70 will change the way heat propagates through a material. In the simplest case, a crack or defect 70 will create an insulation boundary such that the most efficient path for the heat propagating through the material is go around the defect 70. By determining the heat propagation rate in the material, and comparing that to the physical distance between the heating zone and two or more measurement points on the component surface 28 being inspected, the actual path length taken by the heat energy may be determined. Heat going under a defect 70 will increase the path length of the energy path by approximately twice the depth of the crack, thereby slowing the heat transfer at the defect boundary. As a result, an increase of heat occurs on one side of the defect, and a lack of heat is induced on the opposite side of the defect.

The above-described defect inspection system is cost-effective and highly reliable. The system enables a depth of defects to be determined by correlating temperature variations detected in the surface of the component being inspected. As a result, during an inspection of a component surface a depth of each defects is determined to facilitate distinguishing defects that could cause a failure of the component from minor surface anomalies in a cost effective and reliable manner. More specifically, the sensitivity and accuracy of the defect inspection system also enables the detection of other types of defects, such as porosity and/or voids in metals or composites.

Exemplary embodiments of inspection systems are described above in detail. The inspection systems and associated methods of use are not limited to the specific embodiments described herein, but rather, components of each assembly may be utilized independently and separately from other components described herein. Each inspection system component and method of use can also be used in combination with other inspection system components.

While the invention has been described in terms of various specific embodiments, those skilled in the art will recognize that the invention can be practiced with modification within the spirit and scope of the claims.

What is claimed is:

1. A method for detecting a crack extending into a component surface, said method comprising:

positioning a surface of the component to be inspected in an optical path of at least one infrared radiation detector;

heating the component surface using electromagnetic radiation to cause an increase in radiance from a defect present at the component surface;

detecting temperature variations within the component surface using the at least one infrared radiation detector, such that the surface irradiance is measured at predetermined locations across the component surface;

detecting cracks in the component by analyzing radiation transient response data received by the infrared radiation detector; and correlating the temperature variations to the radiation transient response data to determine a depth of the detected cracks.

2. A method in accordance with claim 1 further comprising:

generating a series of video images of the heated surface using the irradiance detected by the infrared radiation detector; and generating a series of graphs plotting irradiance versus distance along the component surface to facilitate determining a peak irradiance intensity level.

3. A method in accordance with claim 2 wherein generating a series of graphs plotting irradiance versus distance further comprises distinguishing component cracks from component minor surface anomalies.

4. A method in accordance with claim 1 wherein detecting temperature variations within the component surface using the infrared radiation detector further comprises:

determining an intensity level of the irradiance; and determining a decay rate of the irradiance intensity level after removing the heat.

5. A method in accordance with claim 1 wherein detecting cracks in the component by analyzing radiation transient response data received by the infrared radiation detector further comprises using a bi-directional scan across the component surface.

6. A method in accordance with claim 1 wherein heating the component surface using electromagnetic radiation further comprises focusing a laser beam on the component surface.

7. A method in accordance with claim 6 wherein focusing a laser beam on the component surface further comprises using a laser beam having at least one of a circular-shaped projection and an S-shaped projection.

8. A method in accordance with claim 6 wherein heating the component surface using electromagnetic radiation further comprises maintaining the laser beam approximately normal to the component surface.

9. A method in accordance with claim 1 wherein detecting cracks in the component further comprises using real time feedback to detect cracks.

10. A method for determining a depth of a crack in a component, said method comprising:

positioning a surface of the component to be inspected in an optical path of at least one infrared radiation detector, such that the optical path is substantially normal to a plane parallel to the component surface;

heating the component surface using electromagnetic radiation to cause an increase in radiance from a defect present in the component surface, such that the heat is applied to the component substantially normal to the component surface;

detecting temperature variations within the component surface using the at least one infrared radiation detector, such that the surface irradiance is measured at predetermined locations across the component surface;

detecting cracks in the component by analyzing radiation transient response data received by the infrared radiation detector; and correlating the temperature variations to the radiation transient response data to determine a depth of the detected cracks.

11. A method in accordance with claim 10 wherein detecting cracks in the component further comprises using real-time feedback to detect the cracks.

12. A method in accordance with claim 10 further comprising generating a series of video images of the heated surface using the irradiance detected by the infrared radiation detector; and digitizing the series of video images to facilitate distinguishing cracks formed in the component surface from minor surface anomalies present in the component surface.

13. A method in accordance with claim 10 further comprising generating a series of graphs plotting irradiance versus distance along the component surface to facilitate determining a peak irradiance intensity level.

14. A method in accordance with claim 10 wherein detecting temperature variations within the component surface detector further comprises:

determining an intensity level of the irradiance; and determining a rate of decay of the irradiance intensity level after removing the heat.

15. A method in accordance with claim 10 further wherein heating the component surface using electromagnetic radiation further comprises focusing a laser beam on the component surface such that the beam is projected with at least one of an S-shape and a circular shape that is expandable.

16. A method in accordance with claim 15 wherein focusing a laser beam on the component surface further comprises using a mask in a Fourier plane to create a desired laser beam shape.

17. A method in accordance with claim 10 wherein focusing a laser beam on the component surface further comprises using a Transverse Electromagnetic Mode (TEM) laser to facilitate beam spatial uniformity and temporal stability.

18. A method in accordance with claim 10 further wherein detecting temperature variations within the component surface using the at least one infrared radiation detector further comprises using a bi-directional scan to facilitate non-perpendicular cracks discrimination.

19. A method in accordance with claim 10 further comprising applying a stress to the component to facilitate detection of any subsurface defects which are proximate to the component surface.

20. A method in accordance with claim 19 wherein applying a stress to the component to facilitate detection of any subsurface defects further comprises applying a stress to the component that is below a characteristic damage threshold stress intensity factor of the component.

* * * * *